US006846220B2

(12) United States Patent
Wakefield

(10) Patent No.: US 6,846,220 B2
(45) Date of Patent: Jan. 25, 2005

(54) ABDOMINAL SUPPORT

(76) Inventor: Wendy May Wakefield, 145 Sladdens Farm Rd., Coopers Creek, Oxford, R.D. (NZ)

( * ) Notice: Subject to any disclaimer, the term of this patent is extended or adjusted under 35 U.S.C. 154(b) by 0 days.

(21) Appl. No.: 10/415,848

(22) PCT Filed: Oct. 31, 2001

(86) PCT No.: PCT/NZ01/00243

§ 371 (c)(1),
(2), (4) Date: Sep. 2, 2003

(87) PCT Pub. No.: WO02/35951

PCT Pub. Date: May 10, 2002

(65) Prior Publication Data

US 2004/0067716 A1 Apr. 8, 2004

(30) Foreign Application Priority Data

Nov. 1, 2000 (NZ) .................................................. 507898

(51) Int. Cl.⁷ .................................................. A41C 1/08
(52) U.S. Cl. .............................. 450/155; 2/92; 128/96.1
(58) Field of Search ......................... 450/1, 155; 2/311, 2/310, 312, 338, 327, 328, 466, 467, 464, 92, 326, 329, 330; 128/869, 873, 874, 96.1, 99.1, 100.1, 101.1; 182/3–5

(56) References Cited

U.S. PATENT DOCUMENTS

| | | | | | |
|---|---|---|---|---|---|
| 2,250,807 A | * | 7/1941 | Lunney | ...................... | 450/113 |
| 3,273,563 A | * | 9/1966 | Bonang | ...................... | 450/155 |
| 3,524,449 A | * | 8/1970 | Peters | ........................ | 450/100 |
| 3,621,849 A | * | 11/1971 | Williams | .................... | 450/155 |
| 4,746,318 A | * | 5/1988 | Moyer | ....................... | 450/155 |
| 4,789,372 A | * | 12/1988 | Wicks | ........................ | 450/155 |
| 4,822,317 A | * | 4/1989 | Wimmer | ...................... | 450/14 |
| 4,836,824 A | * | 6/1989 | Seering et al. | .............. | 450/155 |
| 4,952,192 A | * | 8/1990 | Burke | ........................ | 450/15 |
| 5,702,286 A | * | 12/1997 | Seering et al. | .............. | 450/155 |
| 5,928,059 A | * | 7/1999 | Wicks | ........................ | 450/155 |
| 6,537,123 B2 | * | 3/2003 | Crossman et al. | ............ | 446/83 |

* cited by examiner

Primary Examiner—Gloria M. Hale
(74) Attorney, Agent, or Firm—McCormick Paulding & Huber LLP

(57) ABSTRACT

An abdominal support which includes a pair of shoulder and back straps, each of which passes over one of the wearers shoulders, crosses over the wearer's upper back, and connects to the other shoulder and back strap at the wearer's side; a sling support is secured to each shoulder and back strap at or adjacent the wearers side and a support sling extends from one sling support to the other, passing beneath the wearer's abdomen in use; the sling incorporates length adjusters.

8 Claims, 4 Drawing Sheets

ABDOMINAL SUPPORT

FIELD OF THE INVENTION

The present invention relates to a support for the abdomen. The support of the present invention is especially useful for supporting the distended abdomen during the later months of pregnancy, and will be described with a special reference to this application. However, the support of the present invention also is useful for abdominal support in cases where the abdomen is distended for other reasons e.g., obesity or muscle damage.

BACKGROUND OF THE INVENTION

A distended abdomen, typical of the later months of pregnancy, distorts a woman's posture, putting a strain on her back and upon her abdominal muscles. In the case of pregnancy, the weight of the fetus adds to the problem:- women in their third trimester of pregnancy typically suffer from strained backs and abdominal muscles, together with varicose veins caused by the abnormal pressure on the vascular system. These problems often cause fatigue, and in many cases cause considerable discomfort and even pain.

Over the last 120 years, a number of abdominal supports have been proposed. For example, U.S. Pat. No. 284,831 dated Sep. 11, 1883 discloses a simple sling type of support, with a broad band passing under and over the lower part of the abdomen, supported from shoulder straps. However, the design incorporates very little adjustment:-the only adjustment is the length of each shoulder strap, at a point along the length of the strap above the front of the abdomen. This type of adjustment offers little scope for the very wide range of body sizes and shapes which need to be accommodated, so that a range of different sizes of support would have to be manufactured. Further, the adjustment is such that it tends to pull the abdominal sling upwards over the abdomen:-this does not give optimum support to the abdomen.

U.S. Pat. No. 3,273,563 dated Sep. 20, 1966 discloses a design very similar to that of No. U.S. Pat. No. 284,831, but with the addition of a belt around the wearer's back, presumably to improve support. However, the straps are adjusted in a very similar position to that disclosed in U.S. Pat. No. 284,831, with much the same disadvantages.

U.S. Pat. No. 4,005,715 dated Feb. 1, 1977 also discloses a design generally similar to U.S. Pat. No. 284,831 but with the only adjustment located under each armpit. In fact, the design offers minimal adjustment and appears to rely almost entirely on the elasticity of the material used for providing adequate support.

A number of prior proposals show abdominal supports incorporated into garments:—U.S. Pat. No. 3,621,849 dated Nov. 23, 1971, U.S. Pat. No. 4,789,372 dated Dec. 6, 1988, U.S. Pat. No. 4,835,795 dated Jun. 6, 1989, U.S. Pat. No. 4,746,318 dated May 24, 1988, U.S. Pat. No. 4,822,317 dated Apr. 18, 1989, U.S. Pat. No. 4,952,192 dated Aug. 28, 1990 and U.S. Pat. No. 5,928,059 dated Jul. 27, 1999. In all these patents, a support is incorporated into a girdle (often including a bra) or panty or even incorporated into a bodysuit. The more comprehensive the support, the more complex the adjustments required to make it fit comfortably, and the hotter it is to wear. Since a woman's body generates a great deal of surplus heat during the later months of pregnancy, a support which makes the wearer even hotter is unlikely to prove an advantage, no matter how much support it offers. Further, the garment type of support in most cases would need to be made in a very large range of sizes, to fit all body sizes and types; this very greatly increases the cost of the support.

OBJECT OF THE INVENTION

It is an object of the present invention to provide an abdominal support which is not incorporated into a garment and which is effective in transferring part of the abdominal load to the wearer's shoulders whilst offering a wide range of adjustment to suit the wearer's particular size and shape.

A further object of the present invention is to provide an abdominal support which lifts and cradles the abdominal bulge rather than compressing it, as if the bulge were being supported and lifted by the wearer's own hands. A further object is to provide an abdominal support which can be easily and comfortably adjusted by the wearer in use.

DISCLOSURE OF INVENTION

The present invention provides an abdominal support not incorporated in a garment, said support including a pair of shoulder and back straps, each of which is designed to pass over one of the wearer's shoulders, cross over the wearer's upper back, and connect to the other shoulder and back strap at the wearer's side; a sling support secured to each shoulder and back strap at or adjacent to the wearer's side; and a supporting sling arranged so as to extend from one sling support to the other, passing beneath the wearer's abdomen in use, said sling incorporating length adjustment means.

Said sling length adjustment means may comprise forming the sling as two overlapping portions provided with complementary fasteners, preferably hook and loop fasteners.

Alternatively, said sling length adjustment means is constituted by arranging each end of the sling to pass through the adjacent sling support and be doubled back on itself, each end of the sling being releasably securable to the remainder of the sling, preferably by hook and loop fasteners.

DETAILED DESCRIPTION OF THE PREFERRED EMBODIMENT

By way of example only, a preferred embodiment of the present invention is described in detail with reference to the accompanying drawings, in which:-

Figure 1:
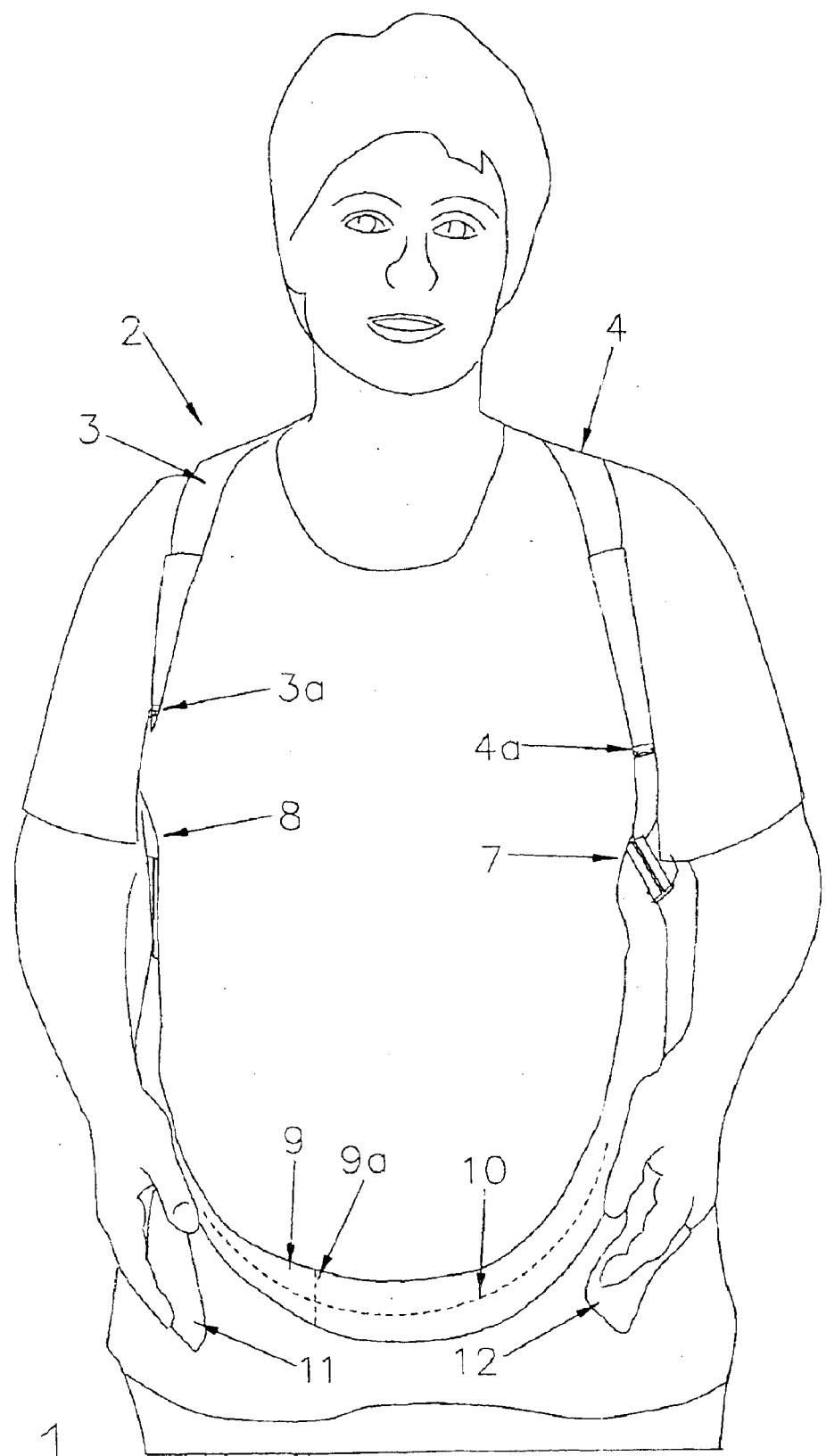
FIG. 1 is a front view of a person wearing the support of the present invention.

Referring to the drawings, a support 2 in accordance with the present invention comprises first and second shoulder straps 3,4, each of which is secured at one end to a corresponding back strap 5,6 and at the other end to a fitting 7,8. The free end of each back strap also is secured to the corresponding fitting 7,8. Thus, the shoulder straps 3,4, back straps 5,6 and fitting 7,8 together form an upper body harness which provides a pair of shoulder straps each of which passes over the wearer's shoulder, across the wearer's upper back, and is secured to the corresponding fitting a short distance below and in front of the wearer's arm on the opposite side to the corresponding shoulder.

Each shoulder strap 3,4 is wide and padded, to spread the load and to avoid any cutting in. Each shoulder strap 3,4 optionally may be adjustable in length, by incorporating a known type of adjusting buckle 3a, 4a. Each back strap 5,6 preferably is made of wide elastic material and may be formed as two separate straps or (as shown) as a combined v-shaped strap.

Figure 2:
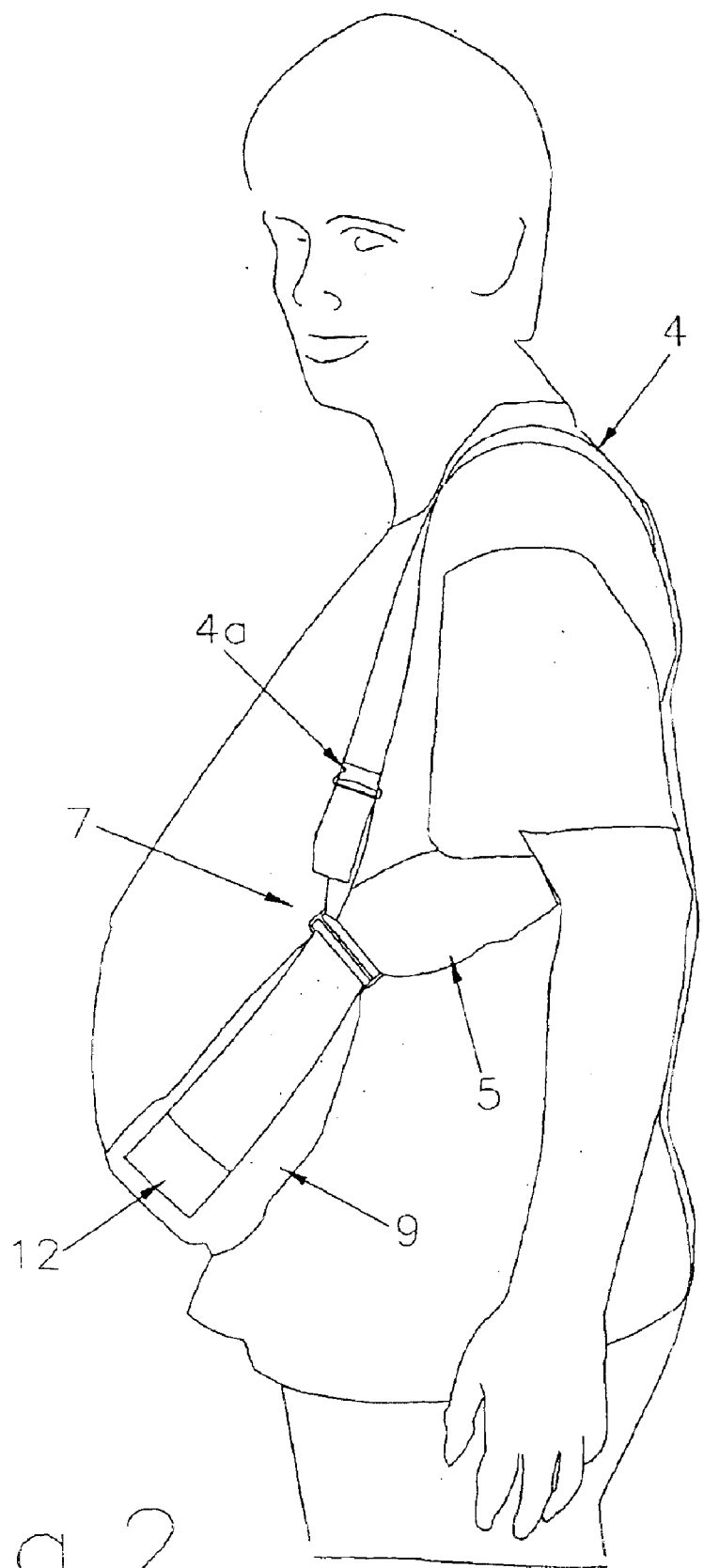
FIG. 2 is a side view of the person of FIG. 1.
Figure 2A:
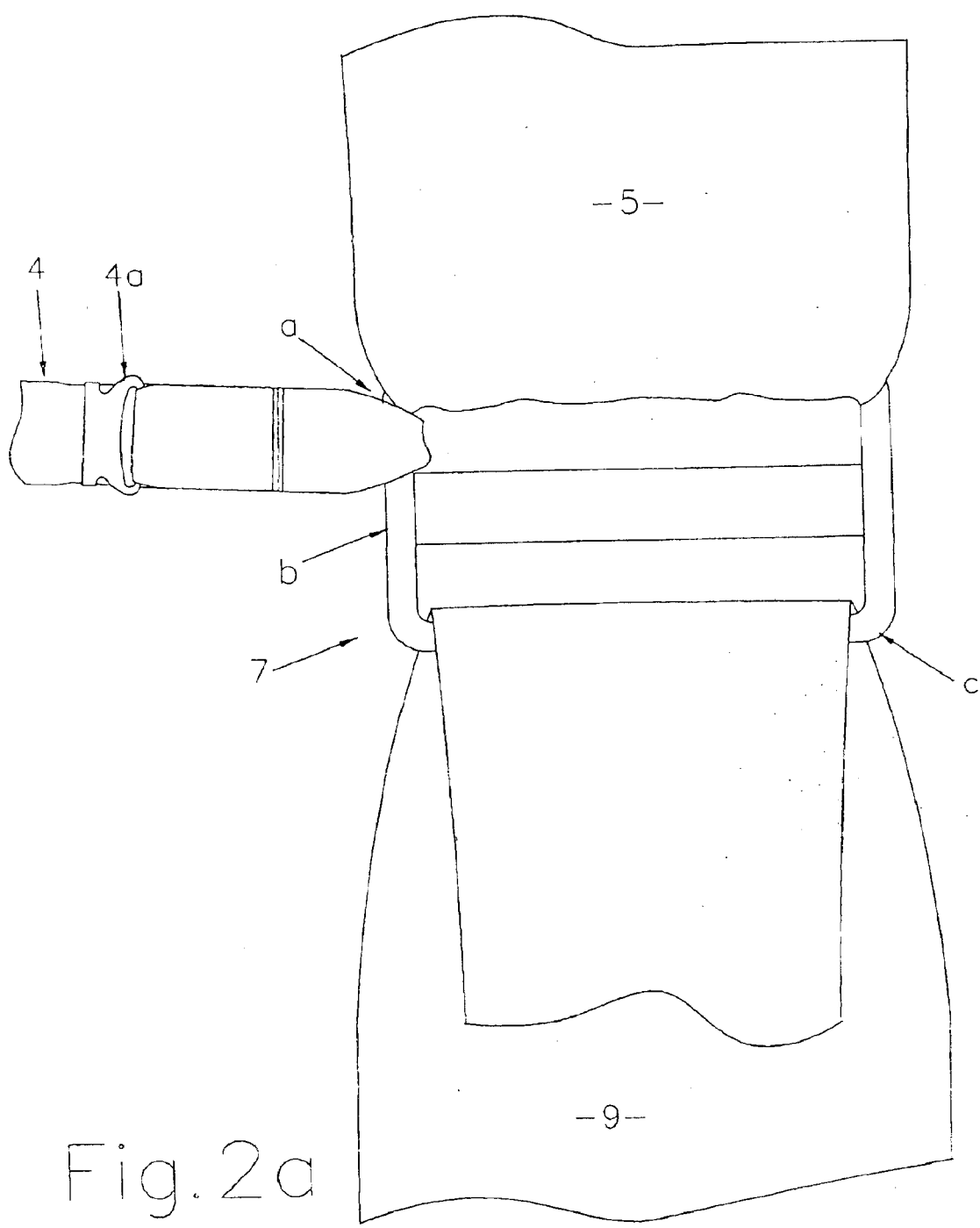
FIG. 2a is a plan view of part of FIG. 2 on an enlarged scale.

Each fitting 7,8 provides an anchorage for the respective end of the shoulder and back straps, and also for the remainder of the support, as hereinafter described. Each fitting 7,8 is a rectangular buckle as shown in detail in FIG. 2a. At each side of the wearer, one end of the back strap 5,6 is secured to one of the long sides a of the respective fitting 8,7, and the end of the shoulder strap 4,3 is secured to a short side b of the fitting 8,7. The straps are secured to the buckle simply by looping the ends of the straps around the buckle and sewing the end to the remainder of the strap.

The lower part of the support comprises a sling 9 in the form of a wide band of suitable material (e.g. cotton fabric) which is of sufficient length to extend from one side of the wearer's abdomen, around the other long side c of the first fitting 7, underneath the lower abdomen of the wearer, around the other long side of the other fitting 8, and down the other side of the wearer's abdomen. Each fitting 7,8 simply needs to provide a secure anchorage for supporting the sling 9, through which the sling can slide and turn back on itself.

The center portion of the sling 9 carries a length of hook and loop fastener 10 on its outer surface, as indicated in broken lines in FIG. 1. The ends of the sling each carry a complementary strip of hook and loop fastener on their underside (not visible). Each end of the sling also carries a mitten or pocket 11, 12 which provides space for the insertion of two or more of the wearer's fingers, as shown in FIG. 1. Alternatively, the mitten or pocket could be formed as a loop.

The above described support is used as follows:- first, the wearer puts on the upper body harness and, if necessary, adjusts the length of the shoulder straps 3,4 so that each fitting 7,8 hangs at the side of the wearer, at a level somewhere between the wearer's bust and waist. The sling 9 is loosely adjusted under the wearer's lower abdomen, so that it lies comfortably underneath the abdominal bulge. The wearer then inserts one hand into each mitten 11, 12 and moves her hands into the position shown in FIG. 1 (i.e. as though supporting the abdominal bulge with her hands) whilst gently pulling on the ends of the sling 9 until the sling gives comfortable but firm support to the abdominal bulge. When the sling is comfortably adjusted, the wearer simply presses the section of hook and loop fastener at the end of each sling under the complementary section of hook and loop fastener 10 on the outer surface of the sling, thus securing the sling at the required length. The wearer then removes her hands from the mittens.

An alternative design for the sling 9 is shown in FIG. 1 only:—In this case, the ends of the sling 9 carrying the mittens 11, 12 are omitted, and the portions of the sling which pass through the fittings 7, 8 are permanently secured to those fittings. The center portion of the sling 9 is formed as two pieces, each carrying a complementary section of hook and loop fastener. The length of the sling is adjusted by the wearer by adjusting the degree of overlap of the two portions of the sling 9; the end of one overlapping portion is indicated by broken lines 9a.

Figure 3:
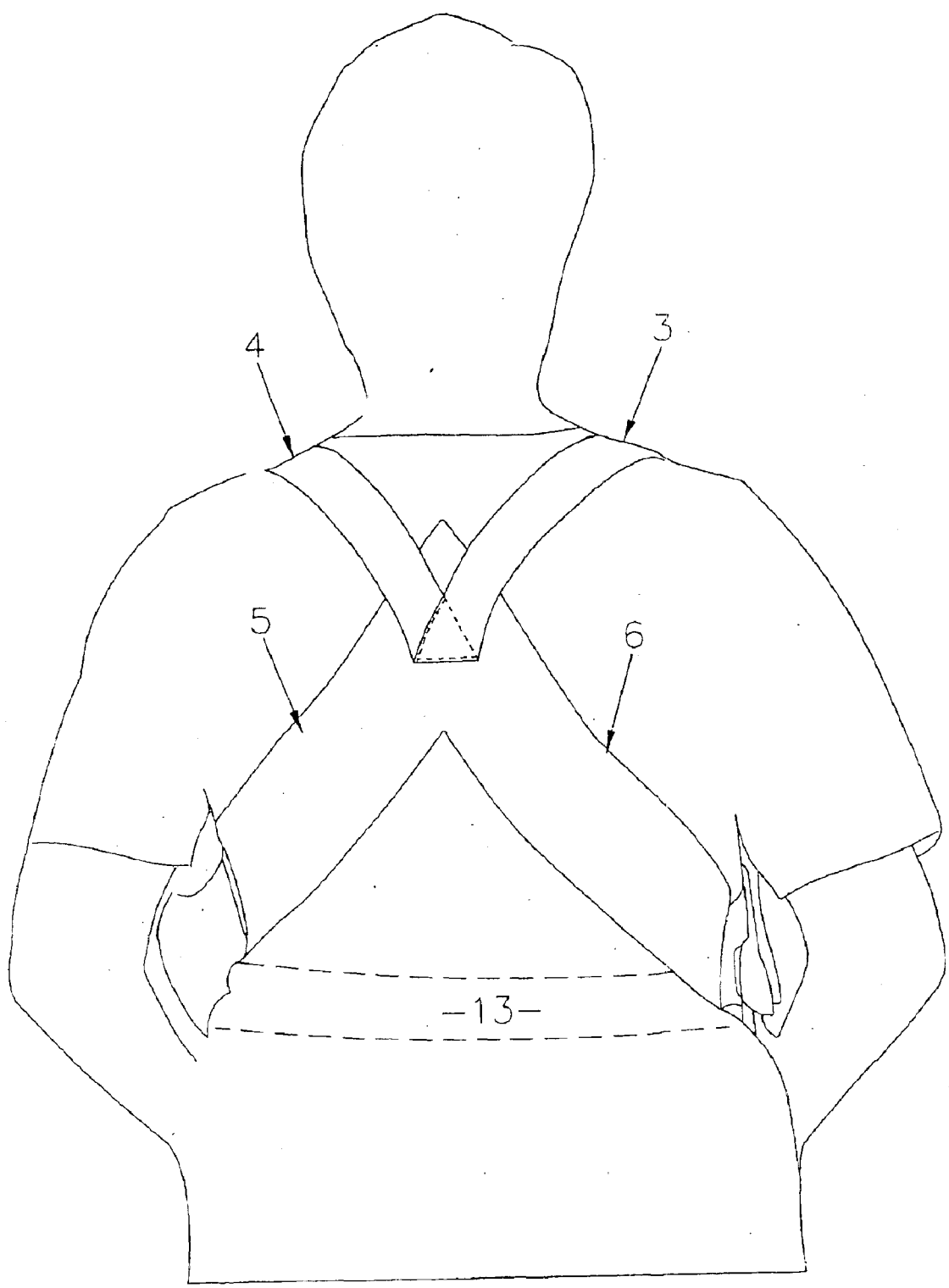
FIG. 3 is a rear view of the person of FIG. 1.

If the wearer requires extra back support, a back waist belt 13 may be fastened between the fittings 7 and 8, across the back of the wearer, as shown in broken lines in FIG. 3. The belt 13 may be made of a single elastic section or two or more sections adjustable in length by means of hook and loop fasteners.

The above described support can be quickly and easily put on or removed or adjusted to give a firmer or less firm support. It will be appreciated that the support transfers much of the weight of the abdominal bulge directly to the shoulders and upper back; this weight is well spread due to the wide shoulder straps and wide, elastic back straps. The crossover design of the back straps prevents the shoulder straps from slipping off the shoulder.

Since the sling is supported only from the sides, it cradles and lifts the abdominal bulge rather than trying to compress it:—this is very much more comfortable for the wearer. Further, because the upper body harness contacts only the shoulders and upper back, the wearer's chest is not constricted in any way.

The support can easily be adjusted to suit a range of body sizes and types.

What is claimed is:

1. An abdominal support not incorporated in a garment, said support including a pair of shoulder and back straps, each of which is designed to pass over one of the wearer's shoulders, cross over the wearer's upper back, and connected to the other shoulder and back straps at the wearer's side; a sling support secured to each shoulder and back strap at or adjacent the wearer's side; and a supporting sling arranged to extend from one sling support to the other, passing beneath the wearer's abdomen in use, said sling incorporating length adjustment means wherein each end of the sling is provided with a mitten, pocket or loop which is arranged to receive the wearer's fingers, to enable the wearer in use to pull on the ends of the sling to adjust the length of the sling under the wearer's abdomen.

2. The abdominal support as claimed in claim 1, wherein said sling length adjustment means is constituted by arranging each end of the sling to pass through the adjacent sling support and be doubled back on itself, each end of the sling being releasably securable to the remainder of the sling.

3. The abdominal support as claimed in claim 1, wherein at least part of the portion of the sling which passes beneath the wearer's abdomen in use is provided with a portion of hook and loop fastener and each end of the sling is provided with a complementary portion of hook and loop fastener, to enable each end of the sling to be secured.

4. The abdominal support as claimed in claim 1, wherein the portion of each shoulder and back strap which passes over the wearer's shoulder in use is padded.

5. The abdominal support as claimed in claim 1, wherein the portion of each shoulder and back strap which passes over the wearer's shoulder in use is adjustable in length.

6. The abdominal support as claimed in claim 1, wherein the portion of each shoulder and back strap which passes across the wearer's back in use is made of an elastic material.

7. The abdominal support as claimed in claim 1, wherein the portion of the shoulder and back straps which passes across the wearer's back in use is formed in one piece.

8. The abdominal support as claimed in claim 1, further comprising an additional back strap securable between said sling supports and in use arranged to pass around the back of the waist of the wearer.

* * * * *